US00PP23925P3

(12) United States Plant Patent
Klemm et al.

(10) Patent No.: US PP23,925 P3
(45) Date of Patent: Sep. 24, 2013

(54) POINSETTIA PLANT NAMED 'NPCW12198'

(50) Latin Name: *Euphorbia pulcherrima* Willd. ex Klotzsch
Varietal Denomination: NPCW12198

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 4 days.

(21) Appl. No.: 13/385,445

(22) Filed: Feb. 21, 2012

(65) Prior Publication Data
US 2013/0219575 P1 Aug. 22, 2013

(51) Int. Cl.
*A01H 5/00* (2006.01)

(52) U.S. Cl.
USPC ..... Plt./307

(58) Field of Classification Search
USPC ..... Plt./307
See application file for complete search history.

*Primary Examiner* — Kent L Bell
(74) *Attorney, Agent, or Firm* — Jondle Plant Sciences Division of Swanson & Bratschun, L.L.C.

(57) ABSTRACT

A new poinsettia plant particularly distinguished by long bracts, high vigor and a slim habit, is disclosed.

1 Drawing Sheet

Genus and species: *Euphorbia pulcherrima* Willd. ex Klotzsch.
Variety denomination: 'NPCW12198'.

BACKGROUND OF THE NEW PLANT

The present invention comprises a new and distinct variety of poinsettia plant, botanically known as *Euphorbia pulcherrima* Willd. ex Klotzsch and hereinafter referred to by the variety name 'NPCW12198'. The new variety is the result of cross conducted in November 2004 in Kenya, district of Nairobi, between the female parent poinsettia plant 'KLEW01066' (U.S. Plant Pat. No. 13,621) and an unnamed male poinsettia plant. A single plant selection was subsequently chosen for further evaluation and asexual propagation.

'NPCW12198' was first propagated via vegetative cuttings in Stuttgart, Germany in October 2005 and has been asexually reproduced by vegetative cuttings in Stuttgart, Germany for over 12 generations. 'NPCW12198' has been found to retain its distinctive characteristics through successive asexual propagations via vegetative cuttings.

'NPCW12198' has not been sold or made publicly available more than one year prior to the filing date of this application.

SUMMARY OF THE INVENTION

The following are the most outstanding and distinguishing characteristics of this new variety when grown under normal horticultural practices in Stuttgart, Germany.

1. Long Bracts;
2. Slim plant habit; and
3. Highly vigorous growth.

DESCRIPTION OF THE PHOTOGRAPH

This new poinsettia plant is illustrated by the accompanying photograph; the colors shown are as true as can be reasonably obtained by conventional photographic procedures.

The photograph is of a whole plant about four-months-old and in full flower.

DESCRIPTION OF THE NEW VARIETY

The following detailed description sets forth the distinctive characteristics of 'NPCW12198'. The data which define these characteristics were collected from asexual reproductions carried out in Stuttgart, Germany. The plant history was taken on four month-old plants grown in 13 centimeter pots from August 2011 to December 2011 with a pinch date at week 31. The plants were grown in a greenhouse covered with glass. Color readings were taken under natural light in the greenhouse. Color references are primarily to The R.H.S. Colour Chart of The Royal Horticultural Society of London (R.H.S.) ($5^{th}$ edition 2007).

DETAILED BOTANICAL DESCRIPTION OF THE NEW PLANT

Classification:
- *Family.*—Euphorbiaceae.
- *Botanical.*—*E. pulcherrima* Willd. ex Klotzsch.
- *Common.*—Poinsettia.

Parentage:
- *Female parent.*—'KLEW01066' (U.S. Plant Pat. No. 13,621).
- *Male parent.*—Unnamed.

Growth:
- *Time to produce a rooted cutting.*—4 weeks.
- *Blooming habit.*—Intermittent.
- *Flowering response time.*—Approximately 52 days.
- *Keeping quality.*—Very good.

Plant:
- *Form.*—Triangular.
- *Growth habit.*—Upright.
- *Height.*—35.0 cm to 40.0 cm.
- *Width.*—Approximately 30.0 cm.

*Number of branches.*—6 to 7.
*Average number of inflorescences per plant.*—6 to 7.

Stems:
*Color.*—Lower part: RHS 146B. Upper part: RHS 143A and RHS 59A.
*Length.*—Approximately 30.0 cm.
*Internode length.*—2.0 cm to 4.0 cm.
*Diameter.*—0.5 cm to 1.0 cm.

Leaves:
*Quantity.*—8 to 15 per lateral branch.
*Arrangement.*—Alternate.
*Shape.*—Ovate.
*Apex.*—Acute.
*Base.*—Rounded.
*Margin.*—Serrated.
*Lobes.*—Quantity: Medium. Lobation characteristics: Medium depth.
*Texture* (*both surfaces*).—Smooth.
*Vein color.*—Upper surface: RHS 59A at base of leaf. Lower surface: RHS N138C.
*Variegation.*—Absent.
*Size.*—Length: 4.0 cm to 10.0 cm. Width: 2.0 cm to 7.0 cm.
*Color.*—Mature foliage: Upper surface: RHS 136A to RHS 139A. Lower surface: RHS 137B. Immature foliage: Upper surface: RHS 144B. Lower surface: RHS 143C.
*Leaf petiole.*—Length: Approximately 2.0 cm to 4.0 cm. Diameter: Approximately 0.2 cm to 0.3 cm. Color: Upper surface: RHS 59A. Lower surface: RHS 59D. Texture: Smooth.

Inflorescence:
*Type and habit.*—Intermittent.
*Lastingness of inflorescence on the plant.*—4 to 5 weeks.
*Diameter.*—Approximately 20.0 cm to 25.0 cm.
*Height.*—2.0 cm to 4.0 cm.
*Fragrance.*—Absent.

Bracts:
*Number of bracts per inflorescence.*—8 to 12.
*Shape.*—Ovate.
*Apex.*—Acute.
*Base.*—Rounded.
*Margin.*—Serrate.
*Lobes.*—Medium.
*Size.*—Length: 8.0 cm to 13.0 cm. Width: 4.0 cm to 6.0 cm.
*Texture* (*both surfaces*).—Smooth.
*Venation pattern.*—Reticulate.
*Vein color.*—Upper surface: RHS 59A. Lower surface: RHS 59D.
*Bract color.*—Upper surface: Between RHS 46B and RHS 46A. Lower surface: RHS 46C.
*Bract petiole.*—Length: 1.0 cm to 3.0 cm. Diameter: 0.2 cm. Color: Upper surface: RHS 59A. Lower surface: RHS 59D.

Cyme:
*Diameter.*—0.5 cm to 2.5 cm.
*Cyathia quantity.*—7 to 10 per inflorescence.
*Cyathium.*—Shape: Ovate. Diameter: 0.3 cm to 0.5 cm. Length: 0.6 cm to 0.7 cm. Color: RHS 143C.
*Peduncle.*—Color: RHS 143C. Diameter: 0.3 cm to 0.4 cm. Length: 0.1 cm to 0.2 cm. Texture: Smooth.
*Nectar cups.*—Shape: Crescentric. Number: 1 per cyathium. Diameter: 0.1 cm when closed, 0.2 cm when open. Length: 0.3 cm to 0.5 cm. Color: RHS 143D when closed, RHS 14C when open.

Reproductive organs:
*Stamens.*—Quantity: 5 to 10 per cyathium. Anther: Shape: Ovate. Length: Less than 0.5 cm. Color: RHS 9A and RHS 12A. Filaments: Length: 0.25 cm. Color: RHS 46A. Pollen: Quantity: Moderate. Color: RHS 9A and RHS 12A.
*Gynoecium.*—Present.
*Pistil quantity per cyathium.*—1.
*Pistil length.*—Approximately 0.2 cm. Stigma: Shape: Divided into 2 parts. Color: RHS 59A. Style: Length: Approximately 0.2 cm. Color: RHS 59A.

Fruit and seed set: No fruit or seed have been observed.
Disease and insect/pest resistance: None specifically tested.

COMPARISON WITH PARENTAL AND COMMERCIAL VARIETIES

'NPCW12198' differs from the female parental poinsettia plant 'KLEW01066' (U.S. Plant Pat. No. 13,621) by having a slim plant habit, whereas 'KLEW01066' has a broader plant habit. Additionally, 'NPCW12198' has average size cyathia, whereas 'KLEW01066' has larger cyathia.

'NPCW12198' differs from the commercial variety 'Dueimviking' (U.S. Plant Pat. No. 20,155) by having an earlier response time and a bract color of medium bright red, whereas 'Dueimviking' has a later response time and a bract color of dark red. Additionally, 'NPCW12198' has bigger and more elongated bracts, whereas 'Dueimviking has medium size bracts.

We claim:

1. A new and distinct cultivar of poinsettia plant named 'NPCW12198' as described and shown herein.

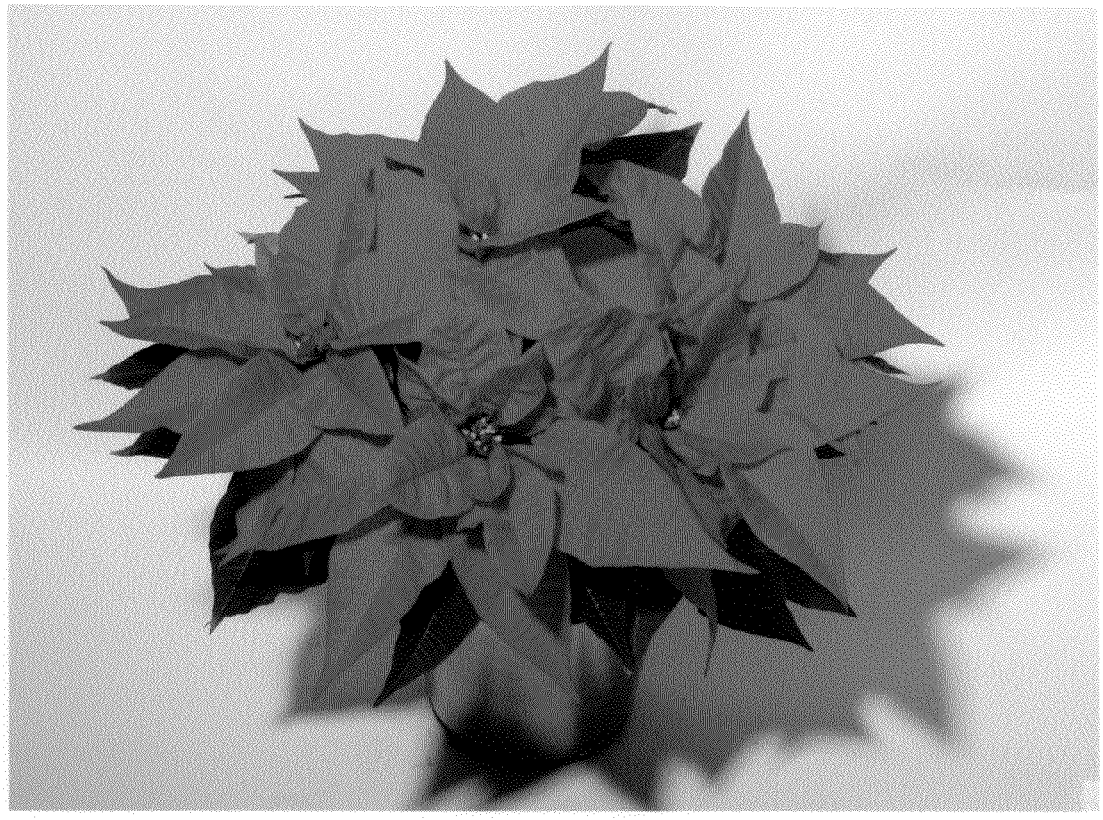

* * * * *